DISPOSABLE PLASTIC BAG

Original Filed Aug. 4, 1964 2 Sheets-Sheet 1

INVENTOR
JOHN C. ILG
BY
Dike, Thompson, Bronstein & Mrose
ATTORNEYS

DISPOSABLE PLASTIC BAG

Original Filed Aug. 4, 1964 2 Sheets-Sheet 2

INVENTOR.
JOHN C. ILG
BY
Dike, Thompson, Bronstein & Mrose
ATTORNEYS

United States Patent Office

Re. 26,674
Reissued Sept. 30, 1969

26,674
DISPOSABLE PLASTIC BAG

John C. Ilg, Fitzwilliam, N.H., assignor to Elliot Laboratories, Inc., Fitzwilliam, N.H., a corporation of New Hampshire Original No. 3,306,327, dated Feb. 28, 1967, Ser. No. 387,367, Aug. 4, 1964. Application for reissue Aug. 9, 1968, Ser. No. 753,815
Int. Cl. A61f *7/04, 7/10;* A61m *3/00*
U.S. Cl. 150—2.1 13 Claims

Matter enclosed in heavy brackets [ ] appears in the original patent but forms no part of this reissue specification; matter printed in italics indicates the additions made by reissue.

*ABSTRACT OF THE DISCLOSURE*

*A disposable, collapsible, flexible, transparent or translucent plastic enema bag having thin, flexible wall panels of thermoplastic sheet material sealed at their peripheries and having a spout of semi-flexible, elastic, yieldable, heat sealable, molded thermoplastic resin which is mounted on a wall panel over a hole in the wall panel, the spout comprising a hollow neck, which is substantially more rigid and thicker than the wall panels, which extends sideways from the wall panel and which is secured to the wall panel in this position by an integral flange, which is sealed flush against the wall panel around the hole, which is thicker and more rigid than the wall panels but which is of substantially lesser thickness and rigidity than the neck, the neck being provided with a removable closure.*

The present invention relates to an improved disposable, flexible and collapsible plastic bag for medical and hospital use, particularly for administering enemas and other fluids and for use as a hot water or ice bag for application to parts of the body. The improved bag of the present invention is of the type having a relatively large neck or spout with a removable closure for filling and emptying the bag and is particularly useful for administering barium or other enemas in which the fluid to be administered contains suspended solids which tend to settle to the bottom of the bag.

Most disposable, collapsible plastic bags are heat sealed around their edges with relatively small inlet and/or outlet tubes extending through a sealed edge or edges, such tubes being of more rigid construction than the collapsible walls of the bag. However, where a relatively large filling and emptying spout is required as in enema bags, ice bags and hot water bags, extending such spout through a sealed edge reduces the collapsibility of the bag and also provides sealing problems. The walls of such bag are much to flexible and collapsible to provide a spout which is integral with the walls of the bag except by providing a relatively thick and more rigid extension forming such a spout. However, this is expensive to do and increases the total cost of the bag too much because the thin, collapsible bag walls conventionally comprise thin expanded sheets of plastic sealed at their edges whereas the thicker and more rigid spout must be of molded plastic. Molding the entire bag with integral spout increases the cost substantially and reduces the flexibility of the walls of the bag at the expense of collapsibility.

It is an object of the present invention to provide an inexpensive, disposable, fully collapsible plastic bag with a one-piece, relatively large, single filling and emptying spout attached to the bag in a novel and simple manner which avoids reduction in collapsibility and the sealing problems referred to above when such spout is passed through a sealed edge of the bag and which permits the use of thin, expanded sheets of plastic for the walls of the bag.

A problem specific to bags used for administering enemas, such as barium enemas, in which the fluid to be administered contains suspended solids, arises from the solids settling to the bottom of the bag to thereby plug the outlet and reduce flow. It is another object of the present invention to provide a disposable, fully collapsible, plastic enema bag in which plugging of the outlet tube by settling solids is avoided.

Another object of the invention is to provide such a disposable, fully collapsible, plastic bag having a disposable part thereof, an improved closure arrangement for closing and sealing the relatively large spout in a simple and inexpensive manner with only a single disposable and removable plastic closure element. The same simple movement of the single closure element locks such closure element in closed position on the spout and effects an excellent seal between closure element and spout without the necessity of additional sealing elements, e.g. sealing rings.

The invention, its objects and its advantages will be more clearly understood from the following description and accompanying drawings describing and showing for illustrative purposes only, an embodiment of the invention.

Figure 1:
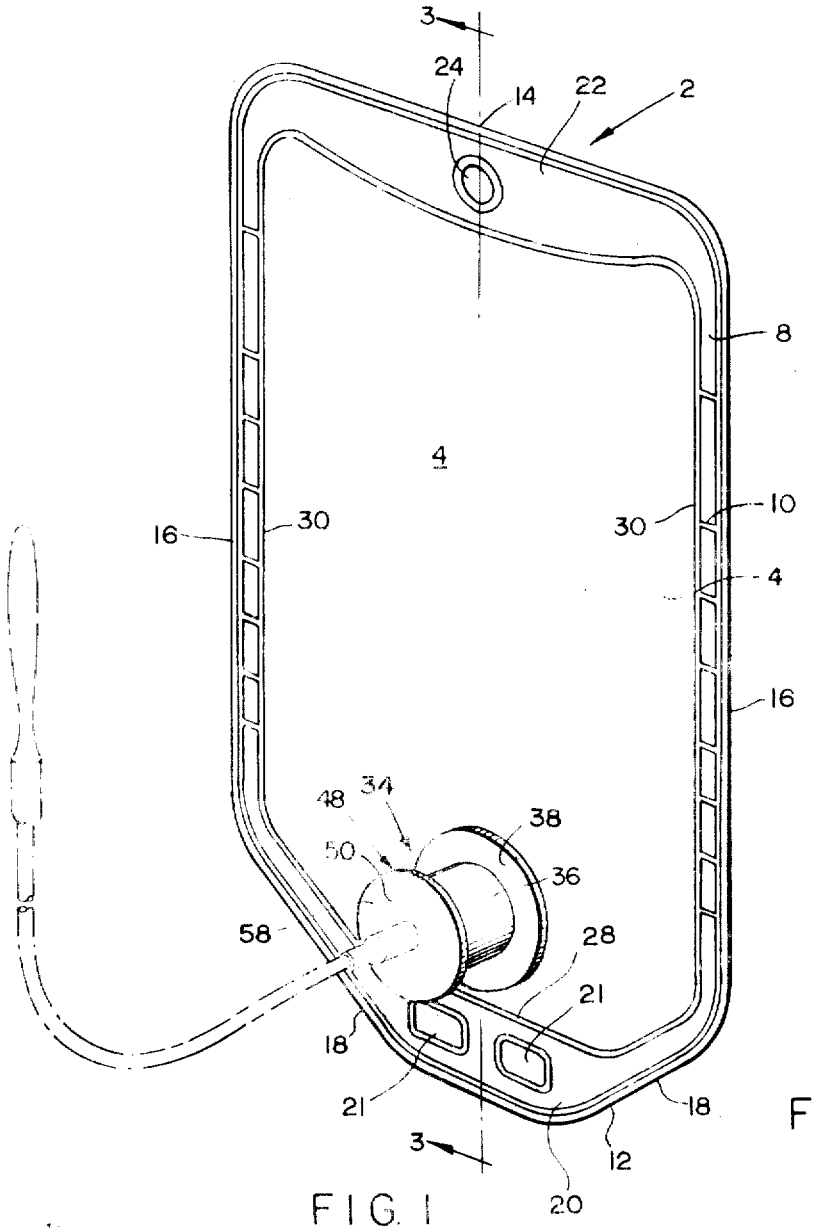
FIG. 1 is a view in perspective of an enema bag embodying the present invention with a conventional enema administering tube and nozzle attached thereto.
Figure 2:
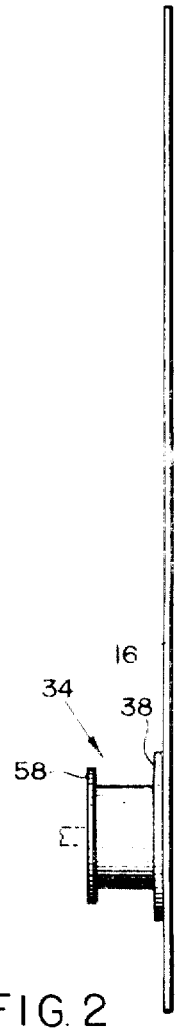
FIG. 2 is a side view of the bag of FIG. 1 with the enema administering nozzle and part of the tubing removed.

With reference to the drawings, 2 represents a disposable, fully collapsible plastic enema bag embodying the present invention.

Bag 2 consists of a pair of thin, flat translucent or transparent, highly flexible and collapsible thermoplastic wall panels 4 and 6, e.g. thin, expanded sheets of polyvinylchloride, normally collapsed flat against each other, as shown, and heat sealed around their entire edges at 8 to form an inner chamber 9. The sealed margin 8 has embossed lines 10 calibrated to indicate the amount of liquid contained in the bag. The embossed lines 10 at one side edge indicate the amount of liquid in the bag when one end 12 is down during enema administration when the bag is being emptied and the embossed lines 10 on the other edge indicate the amount of liquid in the bag on the other side edge indicate the amount of liquid in the bag when the other end 14 is down during filling of the bag. Hereinafter, the edge 12 will be referred to as the lower edge of the bag and the edge 14 will be referred to as the upper edge.

The side edges 16 of the bag taper inwardly at 18 to form the lower end edge 12 of the bag.

The heat seal 8 has a widened portion 20 at the lower edge of the bag, having a pair of openings or holes 21 therethrough for carrying the bag or hanging it while it is being filled. Heat seal 8 also has a widened portion 22 at the upper edge of the bag having an opening or hole 24 therethrough for hanging the bag while it is being emptied. The heat sealing dye sealing the bag panels together at their edges, as shown, is designed to form reinforcing beads along the edges of the holes 21 and 24 and along the edges 12, 16 and 14 of the bag as well as the embossed lines 10.

Wall panel 4 has a hole 26 therein spaced slightly above the lower end 28 of chamber 9 when the bag is in the position shown in FIG. 1 and midway between the sides 30 of the chamber 9. The end 28 of the chamber 9 is the lower end when the bag is being emptied, as shown, but is the upper end when the bag is being filled. Hereinafter, it will be referred to as the lower end of the chamber.

Located over the hole 26 is a hollow filling and emptying spout 34 also of a flexible, yieldable and elastic thermoplastic, e.g. molded polyvinylchloride, having a hollow tubular neck 36 extending sideways from panel 4. Neck 36 has an integral radially outwardly extending flange 38 at its inner end. The inner face 40 of flange 38 is heat sealed flush to the outside of wall panel 4, as shown, around the hole 26 with the hollow neck 36 over the hole.

Although the neck 36 is made of the same material as the wall panels (it need not be), the wall thereof is substantially thicker and hence more rigid than wall panels 4 and 6 but nevertheless it is still relatively flexible and yieldable as well as having elasticity or resilience. It is too rigid to be collapsible like the wall panels. The integral flange 38 is substantially thinner and hence more flexible than the wall of neck 36 but is thicker and hence less flexible than the wall panels 4 and 6.

The outer end portion of the inner surface 39 of tubular neck 36 is tapered radially inwardly at 41 as it extends axially inwardly from the outer edge 42 of the neck to a point 44 intermediate the ends of the neck. The portion 45 of such inner surface 39 from point 44 axially inwardly to the inner end 46 of the passage through the neck is cylindrical in shape.

Figure 3:
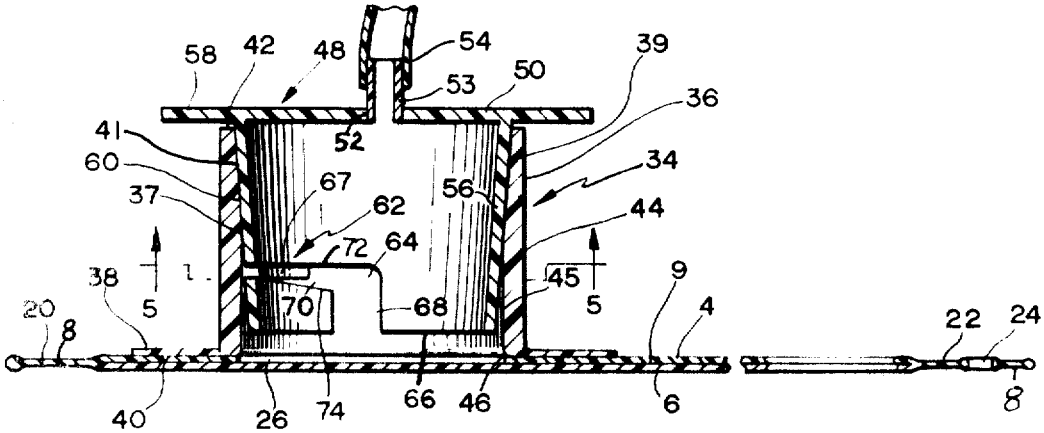
FIG. 3 is a section in elevation taken along the line 3—3 of FIG. 1.
Figure 4:
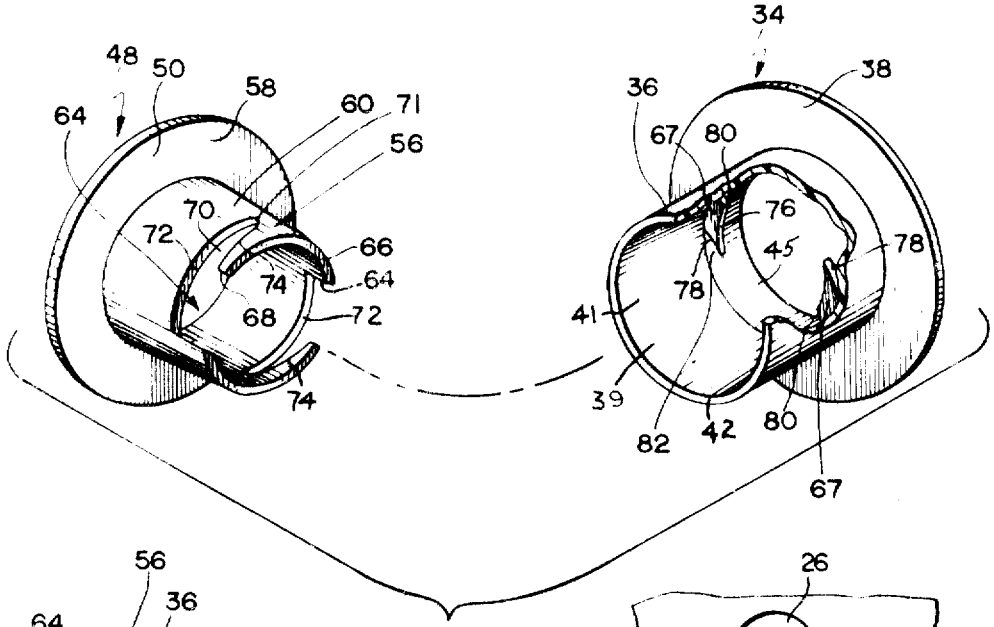
FIG. 4 is an expanded view of the spout and closure cap of the FIG. 1 bag.

A relatively rigid and disposable plastic cap 48, e.g. molded polystyrene, removably closes and seals the spout 34, as shown in FIG. 3. Cap 48 has an end wall 50 having a small hole 52 in the center thereof in which a short piece of plastic tubing 53 is sealed. An end of a length of flexible, plastic, enema tubing 54 (transparent or translucent), is sealed around the piece of tubing 53. The other end of tube 54 has an enema nozzle attached thereto.

Cap 48 has a tubular, tapered side wall 56 depending from end wall 50. Side wall 56 depends from an area of end wall 50 spaced radially inwardly from the periphery of the end wall to form a gripping flange 58. Side wall 56 is adapted to be telescopically received within the tubular neck 36, as shown in FIG. 3.

Side wall 56 tapers radially inwardly as it extends away from end wall 50, i.e. as it extends axially inwardly with respect to neck 36. The taper of the radially outer surface 60 of side wall 56 conforms to the taper 41 of the radially inner surface of the neck 36 so that when the side wall is moved into neck 36, as shown in FIG. 3, it is urged into sealing engagement with the relatively flexible and elastic inner tapered surface 41 of the neck.

The side wall 56 and inner surface 39 of the neck 36 are provided with a bayonet type lock arrangement 62 comprising a pair of opposed L-shaped bayonet slots 64 in the edge 66 of the side wall 56 of the cap and a cooperating pair of opposed bayonet lugs 67 on the inner surface 39 of the neck 36. Each lug 67 consists of a thin flat wall extending integrally and radially inwardly from the inner surface 39 of neck 36 and in a circumferential direction, as shown. The lugs 67 are located where the tapered and cylindrical surfaces 41 and 45 meet.

Each L-shaped slot 64 has a leg 68 extending axially from the edge 66 of side wall 56 and a second leg 70 extending circumferentially at an angle of ninety degrees from leg 68 to form an L-shape. The circumferentially extending, outer (with respect to the bag and neck 36) edge 72 of leg 70 lies in a plane which is perpendicular to the longitudinal axis of side wall 56.

The inner circumferentially extending edge 74 of leg 70 is spirally disposed with respect to the circumference of side wall 56 to thereby provide leg 70 with a narrowing taper as it extends from leg 68 to the narrow end 71.

Figure 5:
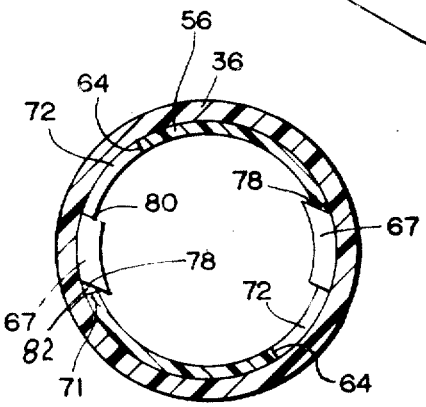
FIG. 5 is a section taken along the line 5—5 of FIG. 3.
Figure 6:
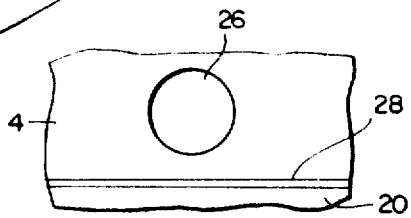
FIG. 6 is a view of a portion of the bag of FIG. 1 with the spout removed to show the opening in the bag wall.

The radially inner edge 76 of each lug wall 67 is arcuate, the arc thereof being concentric with the tubular neck. The leading and trailing end edges 78 and 80, respectively, of each lug wall are parallel and extend circumferentially at an acute angle to the inner surface 39 of the neck, as shown. The acute angle between the leading edge 78 and the inner surface 39 of the neck forms an overhang recess 82. Edge 78 is the leading edge with respect to rotation of the cap 48 to lock and seal position with respect to the neck (counterclockwise as viewed in FIG. 5).

The circumferential dimension of each leg 68 is greater than that of each lug 76 and the width of the narrow end 71 of leg 70 may be about the same or slightly greater than the thickness of the lug wall.

When the side wall 56 of the cap 48 is inserted axially into neck 36, the lugs 67 are moved axially into legs 68 of the slots against the edges 72 of the slots. Upon subsequently rotating the cap and hence the side wall with respect to the neck (in a counter-clockwise direction as viewed in FIG. 5) the lugs 67 are moved circumferentially into the circumferential legs 70 of the slots against the narrow edges 71 of such legs to lock the cap on the neck, as shown in FIG. 3.

When the cap is rotated with respect to the neck, as aforesaid, engagement of the spirally disposed inner edges 74 of the slots with the lugs 67 propel the tapered side wall 56 of the cap axially inwardly into tight sealing engagement with the tapered portion 41 of the relatively flexible inner surface of the neck to form an excellent seal.

The semi-flexibility, yieldability and elasticity of the neck wall provides an excellent sealing effect between the tapered surfaces of the cap and neck.

By providing the portion of inner surface 39 axially inwardly of the lugs with a cylindrical shape, insertion of the cap into the neck and rotation to lock position are facilitated.

By mounting the neck on one of the side panels in the manner shown the bag is made fully collapsible to thereby facilitate and increase flow without the necessity of venting the system. This permits the system to be a fully closed one.

By spacing the hole 26 and spout 34 slightly above the bottom of the interior 9 of the bag, as shown in FIG. 1, a sediment trap is provided below the hole for solid particles which settle to the bottom of the bag to thereby prevent plugging of the outlet and consequent interference with outflow while administering fluids having solid particles suspended therein. The portion of neck 36 below the outlet 52 in the cap also acts as a sediment trap. This is especially important with barium enemas in which the barium compound in the form of solid particles is dispersed in the liquid and tends to settle to the bottom of the bag.

The flat wall design of the bayonet lugs shown in the drawings firmly locks the cap side wall 56 in the neck with such side wall pressed tightly against the flexible inside surface of the neck even though they (the lugs) are integral with the neck and hence are also made of a relatively flexible and yieldable material.

Better sealing is achieved by providing the slots in the cap with the lugs in the neck rather than vice versa since slotting the neck would permit the relatively flexible neck to spread when the cap side wall is forced against the inner surface thereof.

The use of a relatively flexible, heat-sealable plastic spout with mounting flange for mounting on the side of the bag, as described, together with the particular kind of cap described eliminates the necessity of additional sealing elements, since the spout, itself, acts as a seal. Such an arrangement also permits the use of expanded plastic sheets for the walls of the bag and permits the spout to be easily mounted on the bag by a single heat sealing operation without decreasing the collapsibility of the bag so that the fully collapsible bag and closure are made up of only three inexpensive, disposable plastic pieces, namely, the bag, the spout and the cap.

The particular cap design and bayonet locking arrangement shown and described above, i.e. the tapered cap side wall telescopically received in the internally tapered neck, the slots with spiral driving edges in the cap side wall rather than in the neck and the wall design of the lugs integral with the neck, are particularly advantageous with such as relatively flexible spout.

I claim:

1. A disposable, fully collapsible, flexible plastic bag for use as an enema bag, a hot water bag, an ice bag or the like comprising a pair of thin, collapsible, flexible flat wall panels of thermoplastic sheet material normally collapsed against each other and sealed together around their entire peripheries and through which the contents of said bag are visible, a hole in a said wall panel spaced slightly from one edge of the interior of said bag and a substantially greater distance from the opposite edge of said interior, a plastic spout mounted on said wall panel over said hole, said spout comprising a hollow, tubular neck extending sideways from said wall panel and a radially outwardly extending integral flange at the inner end of said neck, a face of said flange being sealed flush to said wall around said hole with said neck over said hole, the wall of said neck being substantially more rigid and thicker than said wall panels, and a removable closure for said neck, said spout being of semi-flexible elastic and yieldable plastic sealed to said plastic wall panel by means of said flange but of substantially greater rigidity and thickness than said wall panels, said closure consisting of a cap having an end wall and a tubular side wall extending therefrom and adapted to be telescopically received within said neck, said side wall being tapered inwardly as it extends away from said end wall, the inner surface of said neck having a taper conforming to the outer taper of said side wall of said cap, whereby when said side wall is moved into said neck the outer tapered surface of said side wall is forced into sealing relation with the inner relatively flexible tapered surface of said neck, said side wall and the inner surface of said neck having bayonet lock means for locking said side wall in said neck with said tapered surfaces of said neck and side wall urged into sealing contact with each other, said bayonet lock means comprising at least a pair of slots in the edge of said cap side wall and at least a pair of integral lugs extending radially inwardly from the inner surface of said neck, said lugs being adapted to be received in said slots, each of said slots extending axially from the edge of said side wall and then in a circumferential direction.

2. A bag according to claim 1, said tubular neck being relatively noncollapsible and the wall thereof being thicker and more rigid than said flange sealed to said bag wall, said flange being thicker and more rigid than said panel walls.

3. A bag according to claim 1, each of said slots being L-shaped, said axially extending portion of said slot comprising one leg of said L-shape and said circumferentially extending portion of said slot comprising a second leg of said L-shape, said first leg of said slot being at least as wide in a circumferential direction as the circumferential dimension of said lug, the axially inner edge of said circumferentially extending second leg of said slot being spirally disposed with respect to said side wall to impart a narrowing taper to said second leg of said slot as it extends circumferentially from said first leg, whereby upon insertion of said cap side wall into said neck said lugs are moved axially into said first legs of said slots and upon subsequent rotation of said side wall in said neck said lugs are moved circumferentially into said second legs of said slots towards the narrow ends of said slots and whereby engagement of said spiral inner edges of said second legs of said slots with said lugs by said rotation propels said tapered side wall of said cap inwardly with respect to said neck into tight sealing contact with said tapered, flexible inner surface of said neck.

4. A bag according to claim 3, the edges of said lug walls adjacent said narrow ends of said second legs of said slots when said lugs are moved circumferentially into said second legs extending at an acute angle to said inner surface of said neck to form overhangs for receiving said narrow ends of said slots.

5. A bag according to claim 1, the taper of said inner surface of said neck extending from the outer end of said neck to said lugs and terminating at said lugs.

6. A bag according to claim 1, said end wall of said cap extending radially outwardly beyond said side wall into a gripping flange.

7. A bag according to claim 1, said end wall having an opening in which is received the end of a flexible tube, said tube being sealed in said opening.

8. A bag according to claim 1, each of said lugs comprising a flat wall extending radially inwardly from the inner surface of said neck and circumferentially with respect to said surface.

9. A bag according to claim 1, each of said lugs being elongated in a circumferential direction, said slots and lugs being respectively located in opposed relation to each other.

10. A bag according to claim 1, the plastic of said spout being heat sealable, said flange being heat sealed to the outer surface of said plastic panel around said hole.

*11. A disposable, collapsible, flexible plastic bag for use as an enema bag, a hot water bag, an ice bag or the like comprising a pair of thin, collapsible, flexible flat wall panels of thermoplastic sheet material normally collapsed against each other and sealed together at their peripheries and through which the contents of said bag are visible, a hole in a said wall panel spaced slightly from one edge of the interior of said bag and a substantially greater distance from the opposite edge of said interior, a plastic spout mounted on said wall panel over said hole, said spout comprising a hollow, tubular neck extending sideways from said wall panel and a radially outwardly extending integral flange at the inner end of said neck, the face of said flange opposite the face from which the the neck extends being sealed flush against the outside of said wall panel around said hole with said neck over said hole, the wall of said neck being substantially more rigid and thicker than said wall panels, said spout being of semi-flexible, elastic, yieldable, heat-sealable, molded, thermoplastic resin sealed to said plastic wall panel by means of said flange, the wall of said tubular neck being thicker and more rigid than said flange sealed to said bag wall, said flange being thicker and more rigid than said wall panels, and a removable closure for said neck.*

*12. A bag according to claim 11, said closure consisting of a cap having an end wall and an annular wall extending therefrom and adapted to be received within said neck, said annular wall having an externally tapered surface, said neck having an internally tapered surface, whereby when said annular wall is moved into said neck, said externally tapered surface thereof is forced into sealing relation with said internally tapered surface of said neck.*

*13. A bag according to claim 12, said cap being relatively rigid compared to said neck.*

References Cited

The following references, cited by the Examiner, are of record in the patented file of this patent or the original patent.

UNITED STATES PATENTS

| | | | |
|---|---|---|---|
| 2,072,225 | 3/1937 | Slater | 150—2.1 |
| 3,205,889 | 9/1965 | Alder et al. | 150—8 X |

| | | | |
|---|---|---|---|
| 841,629 | 1/1907 | Conradson | 215—50 |
| 2,607,383 | 8/1952 | Christophersen | 150—8 |

FOREIGN PATENTS

| | | |
|---|---|---|
| 412,461 | 4/1925 | Germany. |

DONALD F. NORTON, Primary Examiner

U.S. Cl. X.R.

128—227; 150—8